(12) United States Patent
Luethy et al.

(10) Patent No.: US 8,497,293 B2
(45) Date of Patent: Jul. 30, 2013

(54) HALOALKYLSUBSTITUTED ARYLOXYALKYLIMIDAZOLINES FOR USE AS PESTICIDES

(75) Inventors: Christoph Luethy, Munchenstein (CH); Anthony Cornelius O'Sullivan, Stein (CH); Thomas Pitterna, Stein (CH); Jurgen Harry Schaetzer, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 344 days.

(21) Appl. No.: 12/741,896

(22) PCT Filed: Oct. 24, 2008

(86) PCT No.: PCT/GB2008/003604
§ 371 (c)(1),
(2), (4) Date: May 7, 2010

(87) PCT Pub. No.: WO2009/060174
PCT Pub. Date: May 14, 2009

(65) Prior Publication Data
US 2011/0098331 A1    Apr. 28, 2011

(30) Foreign Application Priority Data

Nov. 7, 2007  (GB) .................................. 0721850.6

(51) Int. Cl.
| | |
|---|---|
| *A01N 43/50* | (2006.01) |
| *A01N 33/18* | (2006.01) |
| *C07D 233/14* | (2006.01) |
| *C07C 43/188* | (2006.01) |
| *A01P 3/00* | (2006.01) |
| *A01P 5/00* | (2006.01) |
| *A01P 7/00* | (2006.01) |
| *A01P 7/04* | (2006.01) |

(52) U.S. Cl.
USPC ........................ 514/401; 548/350.1; 514/716

(58) Field of Classification Search
None
See application file for complete search history.

(56) References Cited

U.S. PATENT DOCUMENTS

| 4,226,876 A | 10/1980 | Copp et al. |
|---|---|---|
| 4,228,175 A | 10/1980 | Boeger et al. |
| 4,232,011 A | 11/1980 | Boeger et al. |
| 4,233,306 A | 11/1980 | Boeger et al. |
| 4,241,075 A | 12/1980 | Drabek et al. |
| 5,128,361 A | 7/1992 | Stark et al. |

FOREIGN PATENT DOCUMENTS

| DE | 1935479 | * | 1/1971 |
|---|---|---|---|
| DE | 2940167 | | 4/1980 |
| EP | 0011596 A1 | | 5/1980 |
| EP | 0049797 A2 | | 4/1982 |
| EP | 1958507 A1 | | 8/2008 |
| EP | 1958508 A1 | | 8/2008 |
| FR | 2388496 | * | 11/1978 |
| FR | 2388496 A1 | | 11/1978 |
| GB | 2023603 | | 1/1980 |
| GB | 1592649 | | 7/1981 |
| GB | 1593276 | | 7/1981 |
| JP | 51106739 | | 9/1976 |

* cited by examiner

*Primary Examiner* — Dennis Heyer
(74) *Attorney, Agent, or Firm* — Brian McAlhaney

(57) ABSTRACT

The present invention relates to novel imidazoline derivatives and their use as insecticidal, acaricidal, molluscicidal and nematocidal agents. The invention also extends to insecticidal, acaricidal, molluscicidal and nematicidal compositions comprising such imidazoline derivatives, and to methods of using such derivatives and/or compositions to combat and control insect, acarine, mollusc and nematode pests. A compound of formula (I): and the salts and N-oxides thereof.

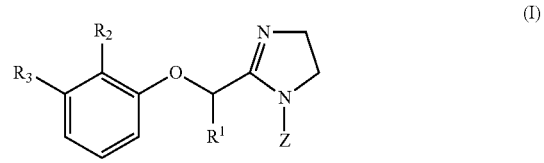

(I)

13 Claims, No Drawings

HALOALKYLSUBSTITUTED ARYLOXYALKYLIMIDAZOLINES FOR USE AS PESTICIDES

This application is a 371 of International Application No. PCT/GB2008/003604 filed Oct. 24, 2008, which claims priority to GB 0721850.6 filed Nov. 7, 2007, the contents of which are incorporated herein by reference.

The present invention relates to novel imidazoline derivatives and their use as insecticidal, acaricidal, molluscicidal and nematocidal agents. The invention also extends to insecticidal, acaricidal, molluscicidal and nematicidal compositions comprising such imidazoline derivatives, and to methods of using such derivatives and/or compositions to combat and control insect, acarine, mollusc and nematode pests.

A number of imidazoline derivatives are known, for example, European Patent Application No. EP 0423802 describes aryloxyalkylimidazolines for pharmaceutical use. Moormann et al., (1990 J. Med Chem 33:614-626) describe 2-[(aryloxy)alkyl]imidazolines as potential antidiarrheals, and disclose the compound 3-(4,5-dihydro-1H-imidazol-2-yl)-3-(2,6-dimethyl-phenoxy)-propan-1-ol.

Aryloxymethylimidazolines for use in combating ectoparasites and/or acarids are known in the prior art, see for example U.S. Pat. No. 5,128,361, U.S. Pat. No. 4,226,876, U.S. Pat. No. 4,414,223, DE 2818367, EP 0011596, U.S. Pat. No. 4,276,302, U.S. Pat. No. 4,232,011, U.S. Pat. No. 4,241,075, U.S. Pat. No. 4,233,306. However, none of these show compounds with a haloalkyl group in position 3 of the phenyl ring in combination with a branched alkylene group between the aryloxy group and the imidazoline ring.

Japanese Patent Application No. JP 51106739 describes specific aryloxymethyl-immidazolines with acaricidal and insecticidal activity.

We have now found further novel imidazoline derivatives, which have surprisingly good pesticidal activity, in particular surprisingly good insecticidal and/or acaricidal activity. Thus according to a first aspect of the invention there is provided a compound of formula (I):

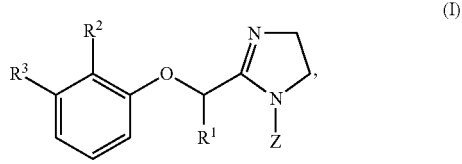

(I)

and salts and N-oxides thereof, wherein
$R^1$ is $C_{1-10}$ alkyl;
$R^2$ is $C_{1-5}$ alkyl, $C_{1-5}$ haloalkyl, $C_{1-5}$ hydroxyalkyl, $C_{2-5}$ alkenyl, $C_{2-5}$ haloalkenyl, $C_{2-5}$ alkynyl, $C_{3-6}$ cycloalkyl, $C_{1-5}$ alkoxy, $C_{1-5}$ haloalkoxy, alkoxy($C_{1-3}$)alkyl, $C_{1-3}$alkoxy($C_{2-3}$)alkenyl, $C_{1-5}$ alkylthio, $C_{1-5}$ haloalkylthio, $C_{1-5}$ alkylsulfinyl, $C_{1-5}$alkylsulfonyl, cyano, nitro, formyl, or the group —CH=N—$R^{18}$ wherein $R^{18}$ is hydroxy or $C_{1-3}$ alkoxy;
$R^3$ is $C_{1-5}$ haloalkyl;
Z is hydrogen, hydroxy, nitro, cyano, rhodano, formyl, G-, G-S—, G-S—S—, G-A-, $R^7R^8$N—, $R^7R^8$N—S—, $R^7R^8$N-A-, G-O-A-, G-S-A-, $(R^{10}O)(R^{11}O)P(X)$—, $(R^{10}O)(R^{11}S)P(X)$—, $(R^{10}O)(R^{11})P(X)$—, $(R^{10}S)(R^{11}S)P(X)$—, $(R^{10}O)(R^{14}R^{15}N)P(X)$—, $(R^{11})(R^{14}R^{15}N)P(X)$—, $(R^{14}R^{15}N)(R^{16}R^{17}N)P(X)$—, G-N=CH—, G-O—N=CH—, N≡C—N=CH—, or Z is compound of formula (II)

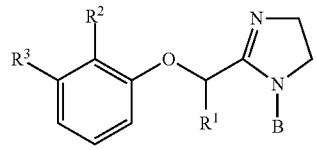

(II)

wherein B is S—, S—S—, S(O)—, C(O)—, or n is an integer from 1 to 6; $R^1$, $R^2$ and $R^3$ are as defined above, and
G is optionally substituted $C_{1-10}$ alkyl, optionally substituted $C_{2-10}$ alkenyl, optionally substituted $C_{2-10}$ alkynyl, optionally substituted $C_{3-7}$ cycloalkyl, optionally substituted $C_{3-7}$ cycloalkenyl, optionally substituted aryl, optionally substituted heteroaryl or optionally substituted heterocyclyl;
A is S(O), $SO_2$, C(O) or C(S);
$R^7$ and $R^8$ are each independently hydrogen or G; or $R^7$ and $R^8$ together with the N atom to which they are attached form a group N=$CR^{12}R^{13}$; or $R^7$ and $R^8$ together with the N atom to which they are attached form a five, six or seven-membered heterocyclic ring, which heterocyclic ring optionally contains one or two further heteroatoms selected from O, N or S, and is optionally substituted by one or two $C_{1-6}$ alkyl groups;
$R^{10}$ and $R^{11}$ are each independently $C_{1-6}$ alkyl, benzyl or phenyl where the phenyl group is optionally substituted with halogen, nitro, cyano, $C_{1-3}$ alkyl, $C_{1-3}$ haloalkyl, $C_{1-3}$ alkoxy, $C_{1-3}$ haloalkoxy;
$R^{12}$, $R^{13}$, $R^{14}$, $R^{15}$, $R^{16}$ and $R^{17}$ are each independently hydrogen or $C_{1-6}$ alkyl;
X is O or S.

For the avoidance of doubt, the term "compound" as used herein includes all salts and N-oxides of said compound, even if not explicitly stated.

The compounds of formula (I) may exist in different geometric or optical isomeric or different tautomeric forms. One or more centres of chirality may be present, for example on the chiral carbon atom $CHR^1$ or a chiral carbon unit in the group G, or a chiral —S(O)— unit in the group Z, in which case compounds of the formula (I) may be present as pure enantiomers, mixtures of enantiomers, pure diastereomers or mixtures of diastereomers. There may be double bonds present in the molecule, such as C=C or C=N bonds, in which case compounds of formula (I) may exist as single isomers of mixtures of isomers. Centres of tautomerisation may be present. This invention covers all such isomers and tautomers and mixtures thereof in all proportions as well as isotopic forms such as deuterated compounds.

Suitable acid addition salts include those with an inorganic acid such as hydrochloric, hydrobromic, sulfuric, nitric and phosphoric acids, or an organic carboxylic acid such as oxalic, tartaric, lactic, butyric, toluic, hexanoic and phthalic acids, or sulphonic acids such as methane, benzene and toluene sulphonic acids. Other examples of organic carboxylic acids include haloacids such as trifluoroacetic acid.

N-oxides are oxidised forms of tertiary amines or oxidised forms of nitrogen containing heteroaromatic compounds. They are described in many books for example in "Heterocyclic N-oxides" by Angelo Albini and Silvio Pietra, CRC Press, Boca Raton, Fla., 1991.

For the avoidance of doubt, unless a group is specifically referred to herein as "optionally substituted" or explicitly as being substituted, said group is to be understood as being unsubstituted.

Each alkyl moiety either alone or as part of a larger group (such as alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, iso-propyl, n-butyl, sec-butyl, iso-butyl, tert-butyl or neo-pentyl. The alkyl groups are suitably $C_1$ to $C_{10}$ alkyl groups, but are preferably $C_{1-8}$, even more preferably $C_{1-6}$ and most preferably $C_{1-4}$ alkyl groups.

Ring or chain forming alkylene, alkenylene and alkinylene groups can optionally be further substituted by one or more halogen, $C_{1-3}$ alkyl and/or $C_{1-3}$ alkoxy.

When present, the optional substituents on an alkyl moiety (alone or as part of a larger group) include one or more of halogen, nitro, cyano, rhodano, isothiocyanato, $C_{3-7}$ cycloalkyl (itself optionally substituted with $C_{1-6}$ alkyl or halogen), $C_{6-7}$ cycloalkenyl (itself optionally substituted with $C_{1-6}$ alkyl or halogen), hydroxy, $C_{1-10}$ alkoxy, $C_{1-10}$ alkoxy($C_{1-10}$)alkoxy, tri($C_{1-4}$)alkylsilyl($C_{1-6}$)alkoxy, $C_{1-6}$ alkoxycarbonyl($C_{1-10}$)alkoxy, $C_{1-10}$ haloalkoxy, aryl($C_{1-4}$)alkoxy (where the aryl group is optionally substituted), $C_{3-7}$ cycloalkyoxy (where the cycloalkyl group is optionally substituted with $C_{1-6}$ alkyl or halogen), $C_{2-10}$ alkenyloxy, $C_{2-10}$ alkynyloxy, mercapto, $C_{1-10}$ alkylthio, $C_{1-10}$ haloalkylthio, aryl($C_{1-4}$)alkylthio (where the aryl group is optionally substituted), $C_{3-7}$ cycloalkylthio (where the cycloalkyl group is optionally substituted with $C_{1-6}$ alkyl or halogen), tri($C_{1-4}$)alkylsilyl($C_{1-6}$)alkylthio, arylthio (where the aryl group is optionally substituted), $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl (where the aryl group may be optionally substituted), tri($C_{1-4}$)alkylsilyl, aryldi($C_{1-4}$)alkylsilyl, ($C_{1-4}$)alkyldiarylsilyl, triarylsilyl, aryl($C_{1-4}$)alkylthio($C_{1-4}$)alkyl, aryloxy($C_{1-4}$)alkyl, formyl, $C_{1-10}$ alkylcarbonyl, hydroxycarbonyl, $C_{1-10}$ alkoxycarbonyl, aminocarbonyl, $C_{1-6}$ alkylaminocarbonyl, di($C_{1-6}$ alkyl)aminocarbonyl, N—($C_{1-3}$ alkyl)-N—($C_{1-3}$ alkoxy)aminocarbonyl, $C_{1-6}$ alkylcarbonyloxy, arylcarbonyloxy (where the aryl group is optionally substituted), $C_{1-6}$alkylaminocarbonyloxy, di($C_{1-6}$)alkylaminocarbonyloxy, oximes and oximethers such as =NO—$C_{1-6}$alkyl, =NO—$C_{1-6}$haloalkyl and =NO—$C_{1-2}$aryl (itself optionally substituted), aryl (itself optionally substituted), heteroaryl (itself optionally substituted), heterocyclyl (itself optionally substituted with $C_{1-6}$ alkyl or halogen), aryloxy (where the aryl group is optionally substituted), heteroaryloxy, (where the heteroaryl group is optionally substituted), heterocyclyloxy (where the heterocyclyl group is optionally substituted with $C_{1-6}$ alkyl or halogen), amino, $C_{1-6}$ alkylamino, di($C_{1-6}$) alkylamino, $C_{1-6}$ alkylcarbonylamino, ($C_{1-6}$)alkylcarbonyl-N—($C_{1-6}$)alkylamino, $C_{2-6}$ alkenylcarbonyl, $C_{2-6}$ alkynylcarbonyl, $C_{3-6}$ alkenyloxycarbonyl, $C_{3-6}$ alkynyloxycarbonyl, aryloxycarbonyl (where the aryl group is optionally substituted) and arylcarbonyl (where the aryl group is optionally substituted).

Alkenyl and alkynyl moieties can be in the form of straight or branched chains, and the alkenyl moieties, where appropriate, can be of either the (E)- or (Z)-configuration. Examples are vinyl, allyl and propargyl. Alkenyl and alkynyl moieties can contain one or more double and/or triple bonds in any combination. It is understood, that allenyl and alkinylalkenyl are included in these terms.

When present, the optional substituents on alkenyl or alkynyl include those optional substituents given above for an alkyl moiety.

In the context of this specification acyl is optionally substituted $C_{1-6}$ alkylcarbonyl (for example acetyl), optionally substituted $C_{2-6}$ alkenylcarbonyl, optionally substituted $C_{3-6}$ cycloalkylcarbonyl (for example cyclopropylcarbonyl, optionally substituted $C_{2-6}$ alkynylcarbonyl, optionally substituted arylcarbonyl (for example benzoyl) or optionally substituted heteroarylcarbonyl (for example nicotinoyl or isonicotinoyl).

Halogen is fluorine, chlorine, bromine or iodine.

Haloalkyl groups are alkyl groups which are substituted with one or more of the same or different halogen atoms and are, for example, $CF_3$, $CF_2Cl$, $CF_2H$, $CCl_2H$, $CH_2F$, $CH_2Cl$, $CH_2Br$, $CH_3CHF$, $(CH_3)_2CF$, $CF_3CH_2$ or $CHF_2CH_2$.

Haloalkenyl groups are alkenyl groups which are substituted with one or more of the same or different halogen atoms.

In the context of the present specification the terms "aryl", "aromatic ring" and "aromatic ring system" refer to ring systems which may be mono-, bi- or tricyclic. Examples of such rings include phenyl, naphthalenyl, anthracenyl, indenyl or phenanthrenyl. A preferred aryl group is phenyl. In addition, the terms "heteroaryl", "heteroaromatic ring" or "heteroaromatic ring system" refer to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl. Preferred examples of heteroaromatic radicals include pyridyl, pyrimidyl, triazinyl, thienyl, furyl, oxazolyl, isoxazolyl, 2,1,3-benzoxadiazole and thiazolyl.

When present, the optional substituents on aryl or heteroaryl are selected independently, from halogen, nitro, cyano, rhodano, isothiocyanato, $C_{1-6}$ alkyl, $C_{1-6}$ haloalkyl, $C_{1-6}$ alkoxy-($C_{1-6}$)alkyl, $C_{2-6}$ alkenyl, $C_{2-6}$ haloalkenyl, $C_{2-6}$ alkynyl, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy($C_{1-10}$)alkoxy, tri($C_{1-4}$)alkyl-silyl($C_{1-6}$) alkoxy, $C_{1-6}$ alkoxycarbonyl($C_{1-10}$)alkoxy, $C_{1-10}$ haloalkoxy, aryl($C_{1-4}$)alkoxy (where the aryl group is optionally substituted with halogen or $C_{1-6}$ alkyl), $C_{3-7}$ cycloalkyoxy (where the cycloalkyl group is optionally substituted with $C_{1-6}$ alkyl or halogen), $C_{2-10}$ alkenyloxy, $C_{2-10}$ alkynyloxy, mercapto, $C_{1-10}$ alkylthio, $C_{1-10}$ haloalkylthio, aryl($C_{1-4}$)alkylthio, $C_{3-7}$ cycloalkylthio (where the cycloalkyl group is optionally substituted with $C_{1-6}$ alkyl or halogen), tri($C_{1-4}$)-alkylsilyl($C_{1-6}$) alkylthio, arylthio, $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl, $C_{1-10}$ alkylcarbonyl, hydroxycarbonyl, $C_{1-10}$ alkoxycarbonyl, aminocarbonyl, $C_{1-6}$ alkylaminocarbonyl, di($C_{1-6}$ alkyl)-aminocarbonyl, N—($C_{1-3}$ alkyl)-N—($C_{1-3}$ alkoxy)aminocarbonyl, $C_{1-6}$ alkylcarbonyloxy, arylcarbonyloxy, $C_{1-6}$alkylaminocarbonyloxy, di($C_{1-6}$)alkylaminocarbonyloxy, aryl (itself optionally substituted with $C_{1-6}$ alkyl or halogen), heteroaryl (itself optionally substituted with $C_{1-6}$ alkyl or halogen), heterocyclyl (itself optionally substituted with $C_{1-6}$ alkyl or halogen), aryloxy (where the aryl group is optionally substituted with $C_{1-6}$ alkyl or halogen), heteroaryloxy (where the heteroaryl group is optionally substituted with $C_{1-6}$ alkyl or halogen), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino, $C_{1-6}$alkylcarbonyl-N—($C_{1-6}$)alkylamino, arylcarbonyl (where the aryl group is itself optionally substituted with halogen or $C_{1-6}$ alkyl), or two adjacent positions on an aryl or heteroaryl system may be cyclised to form a 4, 5, 6 or 7 membered carbocyclic or heterocyclic ring, itself optionally substituted with halogen or $C_{1-6}$ alkyl. Further substituents for aryl or heteroaryl include arylcarbonylamino (where the aryl group is substituted by $C_{1-6}$ alkyl or halogen), $C_{1-6}$alkoxycarbonylamino, $C_{1-6}$alkoxycarbonyl-N—($C_{1-6}$)alkylamino, aryloxycarbonylamino (where the aryl group is substituted by $C_{1-6}$ alkyl or halogen), aryloxycarbonyl-N—($C_{1-6}$)alkylamino (where the aryl group is substituted by $C_{1-6}$ alkyl or halogen), arylsulphonylamino (where the aryl group is substituted by $C_{1-6}$ alkyl or halogen), arylsulphonyl-N—($C_{1-6}$)alkylamino (where the aryl group is substituted by $C_{1-6}$ alkyl or halogen), aryl-N—($C_{1-6}$)alkylamino (where the aryl group is substituted by $C_{1-6}$ alkyl or halogen), arylamino (where the aryl group is substituted by $C_{1-6}$ alkyl or halogen), heteroaryl amino (where the heteroaryl group is substituted by $C_{1-6}$ alkyl or halogen), heterocyclylamino (where the heterocyclyl group is substituted by $C_{1-6}$ alkyl or halogen), aminocarbonylamino, $C_{1-6}$alkylaminocarbonylamino, di($C_{1-6}$)alkylaminocarbonylamino, arylaminocarbonylamino (where the aryl group is substituted by $C_{1-6}$ alkyl or halogen), aryl-N—($C_{1-6}$)alkylaminocarbonylamino (where the aryl group is substituted by $C_{1-6}$ alkyl or halogen), $C_{1-6}$alkylaminocarbonyl-N—($C_{1-6}$)alkylamino, di($C_{1-6}$)alkylaminocarbonyl-N—($C_{1-6}$)alkylamino, arylaminocarbonyl-N—($C_{1-6}$)alkylamino (where the aryl group is substituted by $C_{1-6}$ alkyl or halogen) and aryl-N—($C_{1-6}$)alkylaminocarbonyl-N—($C_{1-6}$)alkylamino (where the aryl group is substituted by $C_{1-6}$ alkyl or halogen).

The terms heterocycle and heterocyclyl refer to a non-aromatic preferably monocyclic or bicyclic ring systems containing up to 10 atoms including one or more (preferably one or two) heteroatoms selected from O, S and N. Examples of such rings include 1,3-dioxolane, oxetane, tetrahydrofuran, morpholine, thiomorpholine and piperazine.

When present, the optional substituents on heterocyclyl include $C_{1-6}$ alkyl and $C_{1-6}$ haloalkyl, an oxo-group (allowing one of the carbon atoms in the ring to be in the form of a keto group), as well as those optional substituents given above for an alkyl moiety.

Cycloalkyl includes cyclopropyl, cyclobutyl, cyclopentyl and cyclohexyl. Cycloalkylalkyl is preferentially cyclopropylmethyl. Cycloalkenyl includes cyclopentenyl and cyclohexenyl.

When present, the optional substituents on cycloalkyl or cycloalkenyl include $C_{1-3}$ alkyl as well as those optional substituents given above for an alkyl moiety.

Carbocyclic rings include aryl, cycloalkyl and cycloalkenyl groups.

For substituted phenyl moieties, heterocyclyl and heteroaryl groups it is preferred that one or more substituents are independently selected from halogen, $C_{1-6}$ alkyl, $C_{1-6}$ haloalkyl, $C_{1-6}$ alkoxy($C_{1-6}$)alkyl, $C_{1-6}$ alkoxy, $C_{1-6}$ haloalkoxy, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{2-6}$ alkenyl, $C_{2-6}$ haloalkenyl, $C_{2-6}$ alkynyl, $C_{3-7}$ cycloalkyl, nitro, cyano, hydroxycaronyl, $C_{1-6}$ alkylcarbonyl, $C_{1-6}$ alkoxycarbonyl, aryl, heteroaryl, $C_{1-6}$ alkylamino, di($C_{1-6}$ alkyl)amino, $C_{1-6}$ alkylaminocarbonyl, or di($C_{1-6}$alkyl) aminocarbonyl.

It is to be understood that dialkylamino substituents include those where the dialkyl groups together with the N atom to which they are attached form a five, six or seven-membered heterocyclic ring which may contain one or two further heteroatoms selected from O, N or S and which is optionally substituted by one or two independently selected ($C_{1-6}$)alkyl groups. When heterocyclic rings are formed by joining two groups on an N atom, the resulting rings are suitably pyrrolidine, piperidine, N-methylpiperazine, thiomorpholine and morpholine each of which may be substituted by one or two independently selected ($C_{1-6}$) alkyl groups.

Preferably the optional substituents on an alkyl moiety include one or more of halogen, nitro, cyano, hydroxycarbonyl, $C_{1-10}$ alkoxy (itself optionally substituted by $C_{1-10}$ alkoxy), aryl($C_{1-4}$alkoxy, $C_{1-10}$ alkylthio, $C_{1-10}$ alkylcarbonyl, $C_{3-5}$ cycloalkylcarbonyl, $C_{1-10}$ alkoxycarbonyl, $C_{1-6}$ alkylaminocarbonyl, di-($C_{1-6}$ alkyl)-aminocarbonyl, $C_{1-6}$ alkylcarbonyloxy, optionally substituted phenyl, heteroaryl, aryloxy, arylcarbonyloxy, heteroaryloxy, heterocyclyl, heterocyclyloxy, $C_{3-7}$ cycloalkyl (itself optionally substituted with ($C_{1-6}$)alkyl or halogen), $C_{3-7}$ cycloalkyloxy, $C_{5-7}$ cycloalkenyl, $C_{1-6}$ alkylsulfonyl, $C_{1-6}$ alkylsulfinyl, tri($C_{1-4}$) alkylsilyl, tri($C_{1-4}$)alkylsilyl($C_{1-6}$)alkoxy, aryldi($C_{1-4}$)alkylsilyl, ($C_{1-4}$)alkyldiarylsilyl and triarylsilyl.

Preferably the optional substituents on alkenyl or alkynyl include one or more of halogen, aryl and $C_{3-7}$ cycloalkyl.

A particularly preferred optional substituent for heterocyclyl is $C_{1-3}$ alkyl.

Preferably the optional substituents for cycloalkyl include halogen, cyano and $C_{1-6}$ alkyl.

The optional substituents for cycloalkenyl preferably include $C_{1-3}$ alkyl, halogen and cyano.

In particularly preferred embodiments of the invention, the preferred groups for $R^1$, $R^2$, $R^3$, and Z, in the compounds of the formula (I), in any combination thereof, are as set out below.

In preferred embodiments $R^1$ is $C_{1-5}$ alkyl. More preferably $R^1$ is $C_{2-4}$ alkyl. Even more preferably R1 is ethyl, n-propyl, n-butyl or i-propyl. Most preferably $R^1$ is ethyl or n-propyl.

In certain embodiments, $R^2$ is $C_{1-5}$ alkyl, $C_{1-5}$ haloalkyl, $C_{2-5}$ alkenyl, $C_{2-5}$ haloalkenyl, $C_{2-5}$ alkynyl, $C_{3-6}$ cycloalkyl, $C_{1-5}$ alkoxy, $C_{1-5}$ haloalkoxy, $C_{1-3}$ alkoxy ($C_{1-3}$) alkyl, $C_{1-5}$ alkylthio, $C_{1-5}$ haloalkylthio, cyano, nitro, or formyl.

In further, preferred embodiments, $R^2$ is $C_{1-2}$ alkyl, c-propyl, $C_{1-2}$ haloalkyl, $C_{2-3}$ alkenyl, $C_{2-3}$ haloalkenyl, or the group —CH=NR$^{18}$ wherein R$^{18}$ is hydroxy or methoxy. Most preferably $R^2$ is methyl.

In preferred embodiments, $R^3$ is $C_{1-2}$ haloalkyl. More preferably $R^3$ is fluoromethyl, difluoromethyl or trifluoromethyl. Most preferably $R^3$ is trifluoromethyl.

In a preferred group of the compounds of the formula (I), Z is hydrogen; cyano; formyl; optionally substituted $C_{1-6}$ alkyl; $C_{3-6}$ alkenyl; $C_{3-6}$ haloalkenyl; $C_{3-6}$alkinyl; $C_{1-6}$ alkylthio; $C_{1-6}$ haloalkylthio; $C_{1-6}$ cyanoalkylthio; optionally substituted phenylthio, said substitution being selected from halogen, nitro, cyano, $C_{1-3}$ alkyl, and $C_{1-3}$ alkoxy; $C_{1-6}$ alkyldithio; di($C_{1-4}$ alkyl)aminothio; optionally substituted $C_{1-6}$ alkylcarbonyl, said substitution being selected from halogen, cyano, and $C_{1-3}$alkoxy; $C_{2-6}$ alkenylcarbonyl; $C_{3-6}$ cycloalkylcarbonyl; optionally substituted phenylcarbonyl, said substitution being selected from halogen, nitro, cyano, $C_{1-3}$ alkyl, and $C_{1-3}$ alkoxy; optionally substituted heteroarylcarbonyl, said substitution being selected from halogen, nitro, cyano, $C_{1-3}$ alkyl, and $C_{1-3}$ alkoxy; $C_{1-6}$ alkoxycarbonyl; $C_{1-6}$ alkylthio-carbonyl; optionally substituted phenylthio-carbonyl, said substitution being selected from halogen, nitro, cyano, $C_{1-3}$ alkyl, and $C_{1-3}$ alkoxy; N,N-di $C_{1-3}$ alkylaminocarbonyl; $C_{1-3}$ alkylaminocarbonyl; $C_{3-5}$ alkenylaminocarbonyl; $C_{3-5}$ alkynylaminocarbonyl; phenylaminocarbonyl wherein said phenyl group is optionally substituted by halogen, nitro, cyano, $C_{1-3}$ alkyl, or $C_{1-3}$ alkoxy; N-phenyl-N-methyl aminocarbonyl wherein said phenyl group is optionally substituted by halogen, nitro, cyano, $C_{1-3}$ alkyl, or $C_{1-3}$ alkoxy; $C_{1-6}$ alkoxythionocarbonyl; $C_{1-6}$ alkylthiothionocarbonyl; phenylthiothionocarbonyl optionally substituted by halogen, nitro, cyano, $C_{1-3}$ alkyl, or $C_{1-3}$ alkoxy; N,N-di $C_{1-3}$ alkylaminothionocarbonyl; $C_{1-3}$ alkylaminothionocarbonyl; phenylaminothionocarbonyl wherein said phenyl group is optionally substituted by halogen, nitro, cyano, $C_{1-3}$ alkyl, or $C_{1-3}$ alkoxy; N-phenyl-N-methyl aminothionocarbonyl wherein said phenyl group is optionally substituted by halogen, nitro, cyano, $C_{1-3}$ alkyl, or $C_{1-3}$ alkoxy; $C_{1-3}$ alkylsulfonyl; haloalkylsulfonyl; $C_{1-3}$ alkenylsulfonyl; phenylsulfonyl optionally substituted by halogen, nitro, cyano, $C_{1-3}$ alkyl, or $C_{1-3}$ alkoxy; N,N-di $C_{1-3}$ alkylaminosulfonyl; di $C_{1-3}$ alkoxy-P(=O)—; di $C_{1-3}$ alkylthio-P(=O)—; di $C_{1-3}$ alkoxy-P(=S)—; di $C_{1-3}$ alkylthio-P(=S)—; ($C_{1-3}$ alkoxy)(phenyl)P(=O)—; ($C_{1-3}$ alkoxy)(phenyl)P(=S)—; $C_{1-3}$ alkyl-N=CH—; $C_{1-3}$ alkoxy-N=CH—; cyano-N=CH—; phenyl-N=CH— wherein said phenyl group is optionally substituted by halogen, nitro, cyano, $C_{1-3}$ alkyl, or $C_{1-3}$ alkoxy; 2-pyridyl-N=CH—; 3-pyridyl-N=CH—; 2-thiazolyl-N=CH—; or a compound of formula (II) wherein B is S— or $CH_2$—; and wherein when Z is an optionally substituted $C_{1-6}$ alkyl group said substitution is selected from: 1-7 fluorine atoms; 1-3 chlorine atoms; 1-3 bromine atoms; a cyano group; 1-2 $C_{1-3}$alkoxy groups; a $C_{1-3}$ haloalkoxy group; a $C_{1-3}$alkylthio group; a $C_{1-3}$ haloalkylthio group; an allyloxy group; a propargyloxy group; a $C_{3-6}$ cycloalkyl group; a phenyl group, wherein said phenyl group is optionally substituted with halogen, nitro, cyano, $C_{1-3}$ alkyl or $C_{1-3}$ alkoxy; a $C_{1-3}$alkylcarbonyloxy group; a $C_{1-3}$ alkoxycarbonyl group; a $C_{1-3}$ alkylcarbonyl group; and an optionally substituted benzoyl, said substitution being selected from halogen, nitro, $C_{1-3}$ alkyl, $C_{1-3}$ alkoxy, and a cyano group.

More preferably, Z is selected from: hydrogen; cyano; formyl; $C_{1-3}$ alkyl; $C_{1-3}$ haloalkyl; $C_{1-3}$ cyanoalkyl; $C_{1-3}$ alkoxy-$C_{1-3}$ alkyl; $C_{1-3}$ benzyloxy-$C_{1-3}$ alkyl; propargyl; $C_{1-6}$ alkylthio; $C_{1-6}$ haloalkylthio; phenylthio optionally substituted with halogen, $C_{1-3}$ alkyl, or $C_{1-3}$ alkoxy; $C_{1-6}$ alkylcarbonyl; phenylcarbonyl optionally substituted by halogen, $C_{1-3}$ alkyl or $C_{1-3}$ alkoxy; $C_{1-6}$ alkoxycarbonyl; $C_{1-3}$ alkylaminocarbonyl; phenylaminocarbonyl wherein said phenyl group is optionally substituted with halogen, $C_{1-3}$ alkyl or $C_{1-3}$ alkoxy; $C_{1-3}$ alkylaminothionocarbonyl; phenylaminothionocarbonyl wherein said phenyl group is optionally substituted by halogen, $C_{1-3}$ alkyl or $C_{1-3}$ alkoxy; $C_{1-3}$ alkylsulfonyl; $C_{1-3}$ haloalkylsulfonyl; di $C_{1-3}$ alkoxy-P(=O)—; $C_{1-3}$ alkoxy-N=CH—; cyano-N=CH—; and 2-pyridyl-N=CH—.

Most preferably, Z is hydrogen.

The compounds described below are illustrative of novel compounds of the invention. Table I provides 56 compounds of formula Ia

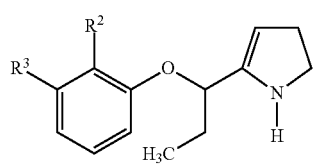

(Ia)

wherein the values of $R^2$ and $R^3$ are given in Table 1.

TABLE 1

| Compound No | $R^3$ | $R^2$ |
|---|---|---|
| I-1 | $CF_3$ | —CN |
| I-2 | $CF_3$ | —$NO_2$ |
| I-3 | $CF_3$ | Me |
| I-4 | $CF_3$ | Et |
| I-5 | $CF_3$ | Pr |
| I-6 | $CF_3$ | iPr |
| I-7 | $CF_3$ | $Cl_2C$=CH— |
| I-8 | $CF_3$ | Vinyl |
| I-9 | $CF_3$ | Allyl |
| I-10 | $CF_3$ | Propargyl |
| I-11 | $CF_3$ | $CF_3$ |
| I-12 | $CF_3$ | $CHF_2$ |
| I-13 | $CF_3$ | $CH_2F$ |
| I-14 | $CF_3$ | $CF_2Cl$ |
| I-15 | $CF_3$ | $CCl_3$ |
| I-16 | $CF_3$ | Cyclopropyl |
| I-17 | $CF_3$ | MeO |
| I-18 | $CF_3$ | $F_3CO$ |
| I-19 | $CF_3$ | $F_2HCO$ |
| I-20 | $CF_3$ | $MeOCH_2$ |
| I-21 | $CF_3$ | MeS |
| I-22 | $CF_3$ | $F_3CS$ |
| I-23 | $CF_3$ | $F_2HCS$ |
| I-24 | $CHF_2$ | —CN |
| I-25 | $CHF_2$ | —$NO_2$ |
| I-26 | $CHF_2$ | Me |
| I-27 | $CHF_2$ | Et |
| I-28 | $CHF_2$ | Vinyl |
| I-29 | $CHF_2$ | $CF_3$ |
| I-30 | $CHF_2$ | $CHF_2$ |
| I-31 | $CHF_2$ | $CH_2F$ |
| I-32 | $CHF_2$ | $CF_2Cl$ |
| I-33 | $CHF_2$ | $CCl_3$ |
| I-34 | $CHF_2$ | cyclopropyl |
| I-35 | $CH_2F$ | —CN |
| I-36 | $CH_2F$ | —$NO_2$ |
| I-37 | $CH_2F$ | Me |
| I-38 | $CH_2F$ | Et |
| I-39 | $CH_2F$ | Vinyl |
| I-40 | $CH_2F$ | $CF_3$ |
| I-41 | $CH_2F$ | $CHF_2$ |
| I-42 | $CH_2F$ | $CH_2F$ |
| I-43 | $CH_2F$ | $CF_2Cl$ |
| I-44 | $CH_2F$ | $CCl_3$ |
| I-45 | $CH_2F$ | cyclopropyl |
| I-46 | $CF_2Cl$ | —CN |
| I-47 | $CF_2Cl$ | —$NO_2$ |
| I-48 | $CF_2Cl$ | Me |
| I-49 | $CF_2Cl$ | Et |
| I-50 | $CF_2Cl$ | Vinyl |
| I-51 | $CF_2Cl$ | $CF_3$ |
| I-52 | $CF_2Cl$ | $CHF_2$ |
| I-53 | $CF_2Cl$ | $CH_2F$ |
| I-54 | $CF_2Cl$ | $CF_2Cl$ |
| I-55 | $CF_2Cl$ | $CCl_3$ |
| I-56 | $CF_2Cl$ | cyclopropyl |

56 Compounds of formula Ib

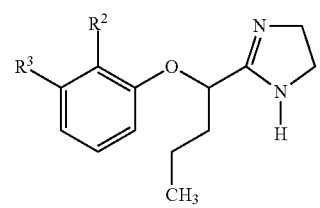

(Ib)

wherein the values of $R^2$ and $R^3$ are as given in Table 1 for compounds I-1 to I-56, are designated as compound Nos. II-1 to II-56, respectively.

56 Compounds of formula Ic

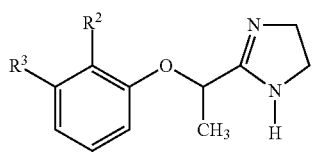

wherein the values of $R^2$ and $R^3$ are as given in Table 1 for compounds I-1 to I-56, are designated as compound Nos. III-1 to III-56, respectively.

56 Compounds of formula Id

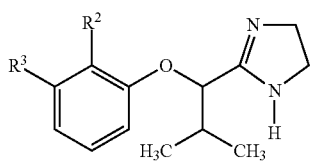

wherein the values of $R^2$ and $R^3$ are as given in Table 1 for compounds I-1 to I-56, are designated as compound Nos. IV-1 to IV-56, respectively.

Table 2 provides 194 compounds of formula Ie

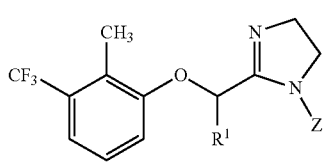

wherein the values of $R^1$ and Z are given in Table 2 below.

TABLE 2

| Compound No | $R^1$ | Z |
|---|---|---|
| V-1 | Et | —CN |
| V-2 | Et | —NO$_2$ |
| V-3 | Et | Me |
| V-4 | Et | Et |
| V-5 | Et | Pr |
| V-6 | Et | Bu |
| V-7 | Et | Allyl |
| V-8 | Et | Isopropenyl |
| V-9 | Et | Vinyl |
| V-10 | Et | but-2-en1-yl |
| V-11 | Et | Propargyl |
| V-12 | Et | but-1-en-1-yl |
| V-13 | Et | but-3-en1-yl |
| V-14 | Et | but-1-en2-yl |
| V-15 | Et | but-2-en2-yl |
| V-16 | Et | but-3-en2-yl |
| V-17 | Et | Methoxymethyl |
| V-18 | Et | Ethoxymethyl |
| V-19 | Et | Propoxymethyl |
| V-20 | Et | Benzyloxymethyl |
| V-21 | Et | 1-methoxyethyl |
| V-22 | Et | 2-methoxyethyl |
| V-23 | Et | —CH$_2$OCOMe |
| V-24 | Et | —CH$_2$OCOEt |
| V-25 | Et | —CH$_2$OCOiPr |
| V-26 | Et | —CH$_2$OCOtBu |
| V-27 | Et | —CH$_2$OCOPh |

TABLE 2-continued

| Compound No | $R^1$ | Z |
|---|---|---|
| V-28 | Et | —CH$_2$OCOOEt |
| V-29 | Et | —CH=N—OMe |
| V-30 | Et | —CH=N—OEt |
| V-31 | Et | —CH=N—Me |
| V-32 | Et | —CH=N—Et |
| V-33 | Et | —CH=N—Ph |
| V-34 | Et | —CH=N-(2-pyridyl) |
| V-35 | Et | —CH=N—C≡N |
| V-36 | Et | —P(O)(OEt)$_2$ |
| V-37 | Et | —P(S)(OEt)$_2$ |
| V-38 | Et | —P(O)(OMe)$_2$ |
| V-39 | Et | —P(S)(OMe)$_2$ |
| V-40 | Et | —P(O)(OPh)$_2$ |
| V-41 | Et | —P(S)(OPh)$_2$ |
| V-42 | Et | —P(O)(OBn)$_2$ |
| V-43 | Et | —P(S)(OBn)$_2$ |
| V-44 | Et | —P(O)(NMe$_2$)$_2$ |
| V-45 | Et | —P(S)(NMe$_2$)$_2$ |
| V-46 | Et | —P(O)(NEt$_2$)$_2$ |
| V-47 | Et | —P(S)(NEt$_2$)$_2$ |
| V-48 | Et | —OH |
| V-49 | Et | —OMe |
| V-50 | Et | —OAc |
| V-51 | Et | —OBz |
| V-52 | Et | SMe |
| V-53 | Et | SCCl$_3$ |
| V-54 | Et | SPh |
| V-55 | Et | S(O)Ph |
| V-56 | Et | S(O)$_2$Me |
| V-57 | Et | S(O)$_2$CF$_3$ |
| V-58 | Et | S(O)$_2$Ph |
| V-59 | Et | C(O)Me |
| V-60 | Et | C(O)Et |
| V-61 | Et | C(O)iPr |
| V-62 | Et | C(O)tBu |
| V-63 | Et | C(O)CH$_2$OMe |
| V-64 | Et | C(O)CH$_2$Cl |
| V-65 | Et | C(O)CHCl$_2$ |
| V-66 | Et | C(O)CCl$_3$ |
| V-67 | Et | C(O)Ph |
| V-68 | Et | C(O)(4-fluorophenyl) |
| V-69 | Et | C(O)(4-chlorophenyl) |
| V-70 | Et | C(O)(4-methoxyphenyl) |
| V-71 | Et | C(O)(2,4-dichlorophenyl) |
| V-72 | Et | C(O)(2,6-dichlorophenyl) |
| V-73 | Et | C(O)(2,6-difluorophenyl) |
| V-74 | Et | C(O)OMe |
| V-75 | Et | C(O)OEt |
| V-76 | Et | C(O)OiPr |
| V-77 | Et | C(O)OtBu |
| V-78 | Et | C(O)OPh |
| V-79 | Et | C(O)O(4-fluorophenyl) |
| V-80 | Et | C(O)O(4-chlorophenyl) |
| V-81 | Et | C(O)O(4-methoxyphenyl) |
| V-82 | Et | C(O)O(2,4-dichlorophenyl) |
| V-83 | Et | C(O)O(2,6-dichlorophenyl) |
| V-84 | Et | C(O)O(2,6-difluorophenyl) |
| V-85 | Et | C(O)NHMe |
| V-86 | Et | C(O)NMe$_2$ |
| V-87 | Et | C(O)NHEt |
| V-88 | Et | C(O)NEt$_2$ |
| V-89 | Et | C(O)NHiPr |
| V-90 | Et | C(O)NHtBu |
| V-91 | Et | C(O)NHPh |
| V-92 | Et | C(O)NH(4-fluorophenyl) |
| V-93 | Et | C(O)NH(4-chlorophenyl) |
| V-94 | Et | C(O)NH(4-methoxyphenyl) |
| V-95 | Et | C(O)NH(2,4-dichlorophenyl) |
| V-96 | Et | C(O)NH(2,6-dichlorophenyl) |
| V-97 | Et | C(O)NH(2,6-difluorophenyl) |
| V-98 | nPr | —CN |
| V-99 | nPr | —NO$_2$ |
| V-100 | nPr | Me |
| V-101 | nPr | Et |
| V-102 | nPr | Pr |
| V-103 | nPr | Bu |
| V-104 | nPr | Allyl |
| V-105 | nPr | Isopropenyl |

TABLE 2-continued

| Compound No | R¹ | Z |
|---|---|---|
| V-106 | nPr | Vinyl |
| V-107 | nPr | Propargyl |
| V-108 | nPr | but-2-en1-yl |
| V-109 | nPr | but-1-en-1-yl |
| V-110 | nPr | but-3-en1-yl |
| V-111 | nPr | but-1-en2-yl |
| V-112 | nPr | but-2-en2-yl |
| V-113 | nPr | but-3-en2-yl |
| V-114 | nPr | Methoxymethyl |
| V-115 | nPr | Ethoxymethyl |
| V-116 | nPr | Propoxymethyl |
| V-117 | nPr | Benzyloxymethyl |
| V-118 | nPr | 1-methoxyethyl |
| V-119 | nPr | 2-methoxyethyl |
| V-120 | nPr | —CH$_2$OCOMe |
| V-121 | nPr | —CH$_2$OCOOEt |
| V-122 | nPr | —CH$_2$OCOiPr |
| V-123 | nPr | —CH$_2$OCOtBu |
| V-124 | nPr | —CH$_2$OCOPh |
| V-125 | nPr | —CH$_2$OCOEt |
| V-126 | nPr | —CH=N—OMe |
| V-127 | nPr | —CH=N—OEt |
| V-128 | nPr | —CH=N—Me |
| V-129 | nPr | —CH=N—Et |
| V-130 | nPr | —CH=N—Ph |
| V-131 | nPr | —CH=N-(2-pyridyl) |
| V-132 | nPr | —CH=N—C≡N |
| V-133 | nPr | —P(O)(OEt)$_2$ |
| V-134 | nPr | —P(S)(OEt)$_2$ |
| V-135 | nPr | —P(O)(OMe)$_2$ |
| V-136 | nPr | —P(S)(OMe)$_2$ |
| V-137 | nPr | —P(O)(OPh)$_2$ |
| V-138 | nPr | —P(S)(OPh)$_2$ |
| V-139 | nPr | —P(O)(OBn)$_2$ |
| V-140 | nPr | —P(S)(OBn)$_2$ |
| V-141 | nPr | —P(O)(NMe$_2$)$_2$ |
| V-142 | nPr | —P(S)(NMe$_2$)$_2$ |
| V-143 | nPr | —P(O)(NEt$_2$)$_2$ |
| V-144 | nPr | —P(S)(NEt$_2$)$_2$ |
| V-145 | nPr | —OH |
| V-146 | nPr | —OMe |
| V-147 | nPr | —OAc |
| V-148 | nPr | —OBz |
| V-149 | nPr | SMe |
| V-150 | nPr | SCCl$_3$ |
| V-151 | nPr | SPh |
| V-152 | nPr | S(O)Ph |
| V-153 | nPr | S(O)$_2$Me |
| V-154 | nPr | S(O)$_2$CF$_3$ |
| V-155 | nPr | S(O)$_2$Ph |
| V-156 | nPr | C(O)Me |
| V-157 | nPr | C(O)Et |
| V-158 | nPr | C(O)iPr |
| V-159 | nPr | C(O)tBu |
| V-160 | nPr | C(O)CH$_2$OMe |
| V-161 | nPr | C(O)CH$_2$Cl |
| V-162 | nPr | C(O)CHCl$_2$ |
| V-163 | nPr | C(O)CCl$_3$ |
| V-164 | nPr | C(O)Ph |
| V-165 | nPr | C(O)(4-fluorophenyl) |
| V-166 | nPr | C(O)(4-chlorophenyl) |
| V-167 | nPr | C(O)(4-methoxyphenyl) |
| V-168 | nPr | C(O)(2,4-dichlorophenyl) |
| V-169 | nPr | C(O)(2,6-dichlorophenyl) |
| V-170 | nPr | C(O)(2,6-difluorophenyl) |
| V-171 | nPr | C(O)OMe |
| V-172 | nPr | C(O)OEt |
| V-173 | nPr | C(O)OiPr |
| V-174 | nPr | C(O)OtBu |
| V-175 | nPr | C(O)OPh |
| V-176 | nPr | C(O)O(4-fluorophenyl) |
| V-177 | nPr | C(O)O(4-chlorophenyl) |
| V-178 | nPr | C(O)O(4-methoxyphenyl) |
| V-179 | nPr | C(O)O(2,4-dichlorophenyl) |
| V-180 | nPr | C(O)O(2,6-dichlorophenyl) |
| V-181 | nPr | C(O)O(2,6-difluorophenyl) |
| V-182 | nPr | C(O)NHMe |
| V-183 | nPr | C(O)NMe$_2$ |
| V-184 | nPr | C(O)NHEt |
| V-185 | nPr | C(O)NEt$_2$ |
| V-186 | nPr | C(O)NHiPr |
| V-187 | nPr | C(O)NHtBu |
| V-188 | nPr | C(O)NHPh |
| V-189 | nPr | C(O)NH(4-fluorophenyl) |
| V-190 | nPr | C(O)NH(4-chlorophenyl) |
| V-191 | nPr | C(O)NH(4-methoxyphenyl) |
| V-192 | nPr | C(O)NH(2,4-dichlorophenyl) |
| V-193 | nPr | C(O)NH(2,6-dichlorophenyl) |
| V-194 | nPr | C(O)NH(2,6-difluorophenyl) |

194 Compounds of formula If

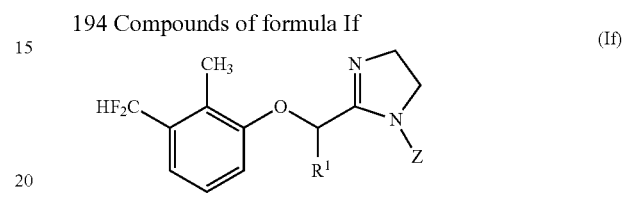

(If)

wherein the values of R¹ and Z are as given in Table 2 for compounds V-1 to V-194, are designated as compound Nos. VI-1 to VI-194, respectively.

194 Compounds of formula Ig

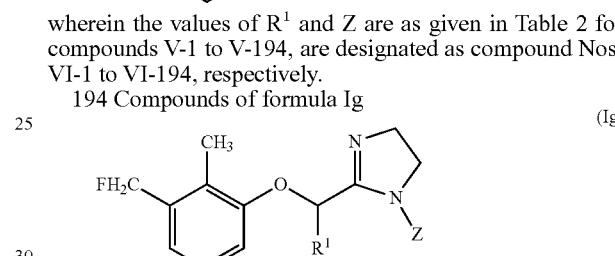

(Ig)

wherein the values of R¹ and Z are as given in Table 2 for compounds V-1 to V-194, are designated as compound Nos. VII-1 to VII-194, respectively.

194 Compounds of formula Ih

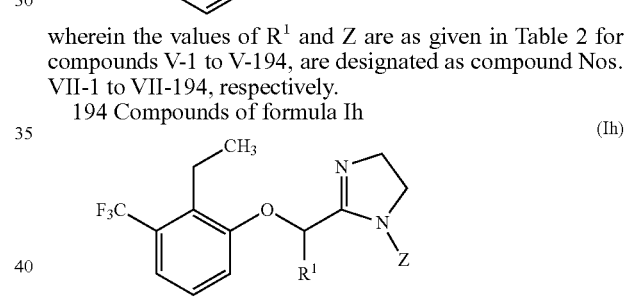

(Ih)

wherein the values of R¹ and Z are as given in Table 2 for compounds V-1 to V-194, are designated as compound Nos. XVIII-1 to VIII-194, respectively.

194 Compounds of formula Ii

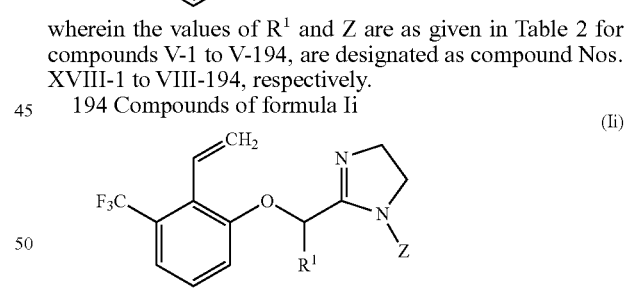

(Ii)

wherein the values of R¹ and Z are as given in Table 2 for compounds V-1 to V-194, are designated as compound Nos. IX-1 to IX-194, respectively.

194 Compounds of formula Ij

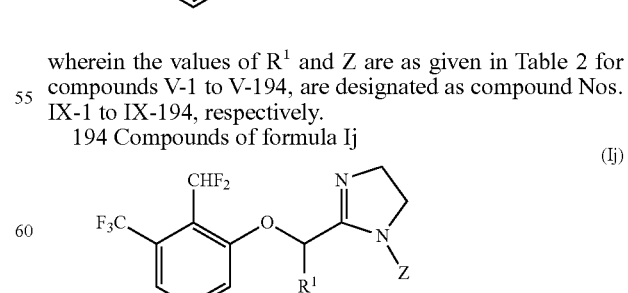

(Ij)

wherein the values of R¹ and Z are as given in Table 2 for compounds V-1 to V-194, are designated as compound Nos. X-1 to X-194, respectively.

Table 3 below provides characterising data for some of the compounds described above; other compounds are only described in this table of characterising data.

TABLE 3

Characterising data for compounds of the invention

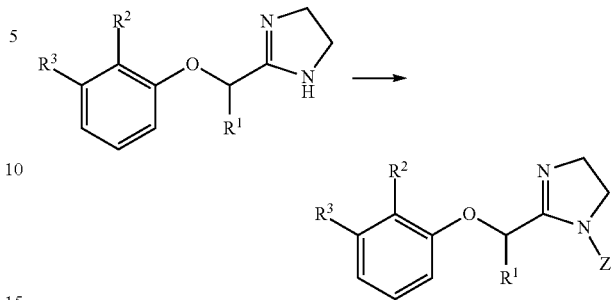

(I)

| compound no | $R^1$ | $R^2$ | $R^3$ | Z | Salt | m.p. [° C.] |
|---|---|---|---|---|---|---|
| 1.001 | Et | Me | $CF_3$ | H | | 125-126 |
| 1.002 | Et | $CHF_2$ | $CF_3$ | H | | 88-91 |
| 1.003 | nPr | Me | $CF_3$ | H | | 106-108 |
| 1.004 | nBu | Me | $CF_3$ | H | | 95-97 |
| 1.005 | iPr | Me | $CF_3$ | H | | 85-89 |
| 1.006 | Et | C≡CH | $CF_3$ | H | | 92-96 |
| 1.007[a)] | Et | CH=NOH | $CF_3$ | H | | gum |
| 1.008 | Et | CH=$CH_2$ | $CF_3$ | H | | 100-105 |
| 1.009 | Et | $CH_2OH$ | $CF_3$ | H | chloride | 150-157 |
| 1.010 | Et | $CH_2OMe$ | $CF_3$ | H | | 128-155 |
| 1.011 | Et | Et | $CF_3$ | H | oxalate | 185-187 |
| 1.012 | nPr | SMe | $CF_3$ | H | maleate | 90-109 |
| 1.013 | Et | $CF_3$ | $CF_3$ | H | | 127-133 |
| 1.014[b)] | nPr | S(O)Me | $CF_3$ | H | | 134-140 |
| 1.015 | nPr | $S(O)_2Me$ | $CF_3$ | H | | 112-120 |
| 1.016 | nPr | Me | $CHF_2$ | H | | 127-128 |
| 1.017 | Et | cPr | $CHF_2$ | H | | 94-100 |
| 1.018[a)] | Et | CH=NOMe | $CF_3$ | H | | 89-99 |
| 1.019 | nBu | Me | $CHF_2$ | H | | 92-93 |
| 1.020 | nBu | Me | $CH_2F$ | H | | 87-88 |
| 1.021 | iPr | Me | $CHF_2$ | H | | 82-84 |
| 1.022 | Et | Me | $CH_2F$ | H | | 77-78 |
| 1.023 | Et | Me | $CHF_2$ | H | | 111-114 |
| 1.024 | nPr | Me | $CH_2F$ | H | | 84-85 |
| 1.025[c)] | Et | CH=CHMe | $CF_3$ | H | | 64-67 |
| 1.026[c)] | Et | CH=CHBr | $CF_3$ | H | | 91-124 |
| 1.027[c)] | Et | CH=CHOMe | $CF_3$ | H | maleate | 98-110 |
| 1.028 | nPr | Me | $CF_3$ | H | chloride | 173-175 |

[a)] E or Z form
[b)] Single enantiomer pair
[c)] E and Z form

Compounds of the invention can be prepared by a variety of methods, for example those described below.

Compounds of the formula I in which Z is not H can be prepared from compounds of the formula I in which Z is H, by treatment with the appropriate reagent. Depending on the nature of Z this can be for example an alkylating agent, an acylating agent, a carbamoylating agent, a phosphorylating agent, a sulfenylating agent or an oxidising agent. These derivatisating agents are generally electrophiles. Methods for the conversion of NH groups into NZ groups can be found for example in T. W. Greene and P. G. M. Wuts "Protecting Groups in Organic Synthesis" 3rd Edition, Wiley, N.Y. 1999.

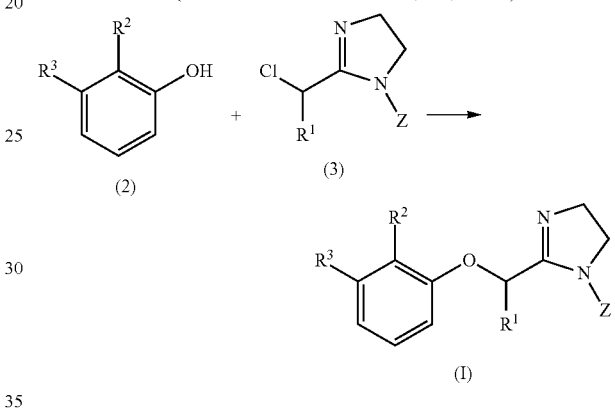

Compounds of the formula I can be prepared by alkylation of a phenol of the formula 2, with a 2-haloalkylimidazoline of the formula 3 (J. Am. Chem. Soc. 1947, 69, 1688).

Compounds of the formula I can be prepared from nitriles of the formula 4, by treatment with a diamine of the formula 5, wherein Z has the meanings assigned to it above. This is advantageously performed in the presence of a catalyst such as $CS_2$, $P_2S_5$ (J. of Med. Chem., 2003 46, 1962) or $Na_2S_4$ (DE 2512513). The nitrile 4 can be converted to imidates of the formula 6 using an alcohol such as methanol and a catalytic amount of base such as NaOH, or to salts of imidate of formula 6 using an alcohol such as methanol or ethanol and an acid such as HCl. Imidates of the formula 6 can be converted to compounds of the formula I on treatment with diamines of the formula 5 (J. of Med. Chem., 2004,47, 6160; J. Am. Chem. Soc. 1947, 69, 1688). Nitriles of the formula 4 can be prepared by alkylating phenols of the formula 2 with a nitrile of the formula 8, bearing a leaving group $L_1$ (J. Am. Chem. Soc. 1947, 69, 1688).

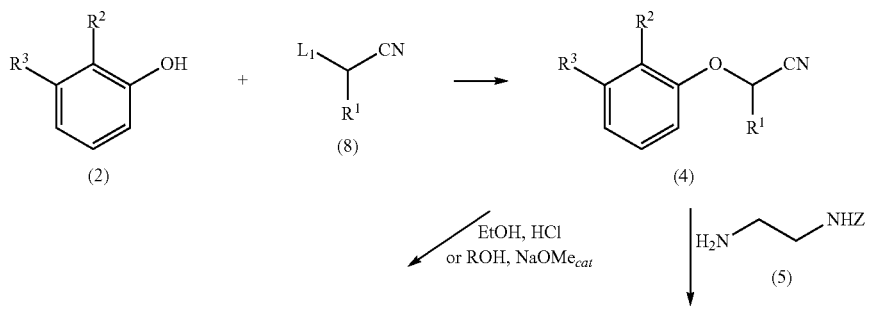

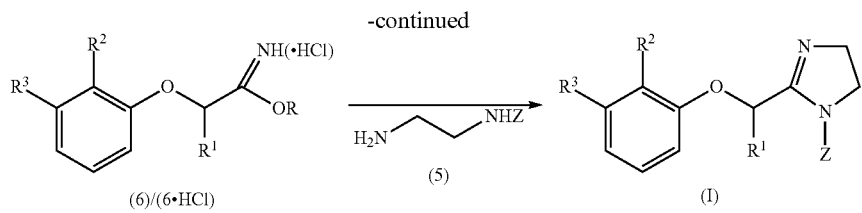

The compounds of the formula 4, wherein $R^1$ is $C_{1-10}$ alkyl; $R^2$ is $C_{1-5}$ alkyl, $C_{1-5}$ haloalkyl, $C_{2-5}$ alkenyl, $C_{2-5}$ haloalkenyl, $C_{2-5}$ alkynyl, $C_{3-6}$ cycloalkyl, $C_{1-5}$ alkoxy, $C_{1-5}$ haloalkoxy, $C_{1-3}$ alkoxy($C_{1-3}$)alkyl, alkylthio, $C_{1-5}$ haloalkylthio, cyano, nitro or formyl; and $R^3$ is $C_{1-5}$ haloalkyl, hydroxy-$C_{1-6}$alkyl, or formyl have been specifically designed as intermediates for the synthesis of the compounds of the formula I and thus form yet a further aspect of the invention.

TABLE 4

Characterising data for compounds of the invention (4)

| compound number | $R^1$ | $R^2$ | $R^3$ | Physical data |
|---|---|---|---|---|
| 4.001 | $CH_2CH_3$ | Me | $CF_3$ | Oil |

Esters of the formula 7 can be converted to imidazolines of the formula I by treatment with diamines of the formula 5 (J. Am. Chem. Soc. 1950, 72, 4443-5). Alkylaluminium reagents can be used with advantage to facilitate this reaction. This conversion occurs in two steps by forming first the monoamide 10, which can serve as a precursor to imidazolines of the formula I. Esters of the formula 7 can be prepared by alkylation of phenols of the formula 2 with esters of the formula 9, wherein $L_2$ is a leaving group, and Rxx is an optionally substituted alkyl or aryl group (typically $C_{1-6}$ alkyl, phenyl or benzyl).

The leaving groups $L_1$ and $L_2$ are typically those used for $S_N2$ reactions. $L_1$ and $L_2$ become anions of organic or inorganic acids on leaving their substrates 8 and 9. Typical leaving groups are for example halide like chlorine or bromine, alkylsulfonates like mesylate, and arylsulfonates like p-tosylate.

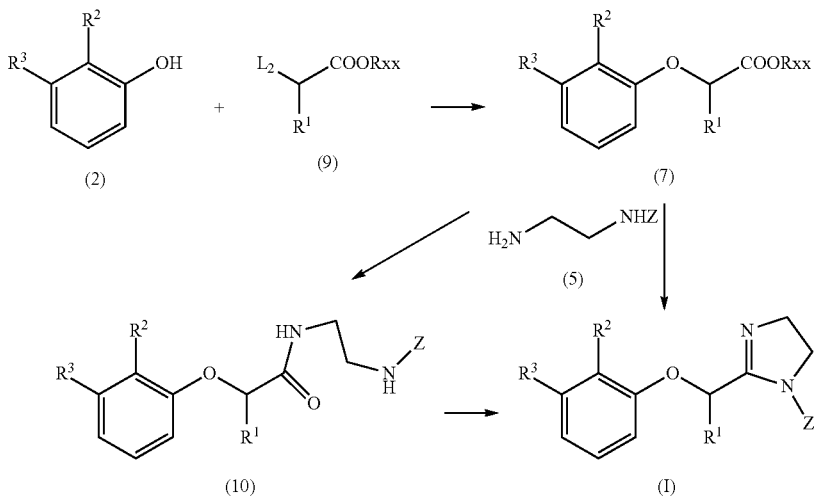

Compounds of the formula I can be prepared from imidazolines of the formula 11 by introduction of a group $R^1$. This can be done by treating 11 with a base and then subsequently with an electrophile capable of introducing the group $R^1$. A typical electrophile could be a halide such as $R^1$—Cl, $R^1$—Br, or $R^1$—I. A typical base could be n-butyllithium or mesityl-lithium. The Z group can be a protecting group such tBuOC(O) or $(CH_3)_3$Si, which can be removed if desired, and a different Z group can be attached as described above if so desired.

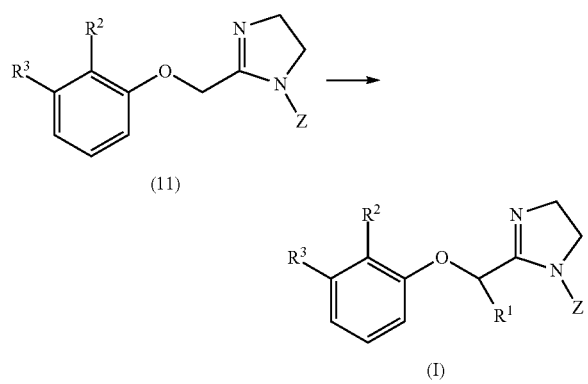

Compounds of formula (2), (3), (5), (8) and (9) are known compounds or may be obtained readily from known compounds using processes that are routine in the art and with which the skilled man will be familiar. Compounds of the formula (11) wherein $R^3$ and Z are as defined hereinbefore, and $R^2$ is $C_{2-5}$alkyl, $C_{1-5}$ haloalkyl, $C_{2-5}$ alkenyl, $C_{2-5}$ haloalkenyl, $C_{2-5}$ alkynyl, $C_{3-6}$ cycloalkyl, $C_{1-5}$ alkoxy, $C_{1-5}$ haloalkoxy, $C_{1-3}$ alkoxy($C_{1-3}$)alkyl, $C_{1-5}$ alkylthio, $C_{1-5}$ haloalkylthio, cyano, nitro, or formyl, are novel. These novel intermediates form yet a further aspect of the invention.

In a second aspect of the invention the compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarid, nematode and mollusc pests. Insects, acarids, nematodes and molluscs are hereinafter collectively referred to as pests.

By the terms "combat" or "combating" it is meant that compounds of formula (I) may be used to prevent or inhibit infestation by a pest of a crop or locus of a crop. Levels of infestation may be measured by any appropriate method known in the art. An inhibition of infestation is observed where the level of infestation is lower in a crop/locus of a crop treated with a compound of formula (I) in comparison to the level of infestation observed or predicted in a crop/locus of a crop that has not been treated with a compound of formula (I).

By the terms "control" or "controlling" it is meant that, pests are repelled, are unable to feed, are unable to reproduce, and/or are killed. Thus the method of the invention may involve the use of an amount of the active ingredient that is sufficient to repel said pests (i.e. a repellently effective amount of active ingredient), an amount of the active ingredient that is sufficient to stop pests feeding, an amount of the active ingredient that is sufficient to inhibit reproduction (e.g. by inhibiting oviposition or ovulation, or by mediating an ovicidal effect), or it may involve the use of an insecticidally-, nematocidally- or molluscidally-effective amount of active ingredient (i.e. an amount sufficient to kill said pests), or the method of the invention may involve any combination of the above effects.

The pests which may be combated and controlled by the use of the invention compounds include those pests associated with agriculture (which term includes the growing of crops for food, fuel, and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (*thrips*), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus, Reticulitermes flavipes, R. speratu, R. virginicus, R. hesperus*, and *R. santonensis*) and the Termitidae (for example *Globitermes sulphureus*), *Solenopsis geminata* (fire ant), *Monomorium pharaonis* (pharaoh's ant), *Damalinia* spp. and *Linognathus* spp. (biting and sucking lice), and *Deroceras reticulatum* (slug).

The invention therefore provides a method of combating and controlling insects, acarids, or molluscs which comprises applying an insecticidally, acaricidally, or molluscicidally effective amount of a compound of formula (I), or a composition containing a compound of formula (I), to a pest, a locus of pest, or to a plant susceptible to attack by a pest. The compounds of formula (I) are preferably used against insects or acarines.

The term "plant" as used herein includes seeds, seedlings, bushes and trees.

In particularly preferred embodiments, compounds of formula (I) and compositions containing such compounds are used in methods of controlling and combating insects in the orders Hemiptera, Lepidoptera, Coleoptera, Thysanoptera, Diptera, Blattodea, Isoptera, Siphonaptera, Hymenoptera, and/or Orthoptera. In certain embodiments, such compounds and compositions are particularly useful in controlling and combating Hemiptera, Lepidoptera, Coleoptera, Thysanoptera, or Diptera. In further embodiments such compounds and compositions are particularly useful in controlling and combating Lepidoptera, Thysanoptera, Isoptera, Siphonaptera, Hymenoptera, or Orthoptera. It is particularly preferred that compounds of formula (I), and compositions containing these compounds are used against Hemipteran insects.

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). Suitable inert diluents or carriers are described herein, for example with respect to certain formulation types, and thus the term includes solid diluents, inorganic water soluble salts, water-soluble organic solids and the like as well as simple diluents such as, for example, water and/or oils. SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

In a still further aspect the invention provides a method of combating and controlling pests at a locus which comprises treating the pests or the locus of the pests with an insecticidally, acaricidally, nematicidally or molluscicidally effective amount of a composition comprising a compound of formula (I). Such compositions are preferably used against insects, acarids or nematodes.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder: Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water. In particularly preferred embodiments, compounds of formula I will be formulated as an EC or EW formulation.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurised, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilisers (for example nitrogen-, potassium- or phosphorus-containing fertilisers). Suitable formulation types include granules of fertiliser. The mixtures suitably contain up to 25% by weight of the compound of formula (I).

The invention therefore also provides a fertiliser composition comprising a fertiliser and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (i); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;
b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;
c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;
d) Benzoyl ureas, such as diflubenzuron, triflumuron, hexaflumuron, flufenoxuron or chlorfluazuron;
e) Organic tin compounds, such as cyhexatin, fenbutatin oxide or azocyclotin;
f) Pyrazoles, such as tebufenpyrad and fenpyroximate;
g) Macrolides, such as avermectins or milbemycins, for example abamectin, emamectin benzoate, ivermectin, milbemycin, spinosad or azadirachtin;
h) Hormones or pheromones;
i) Organochlorine compounds such as endosulfan, benzene hexachloride, DDT, chlordane or dieldrin;
j) Amidines, such as chlordimeform or amitraz;
k) Fumigant agents, such as chloropicrin, dichloropropane, methyl bromide or metam;
l) Neonicotinoid compounds such as imidacloprid, thiacloprid, acetamiprid, nitenpyram, thiamethoxam or sulfoxaflor;
m) Diacylhydrazines, such as tebufenozide, chromafenozide or methoxyfenozide;
n) Diphenyl ethers, such as diofenolan or pyriproxifen;
o) Indoxacarb;
p) Chlorfenapyr; or
q) Pymetrozine, in particular pymetrozine dihydrate;
r) Tetronic acids such as spirotetramat, spirodiclofen, spiromesifen;
s) Spinosyns, such as spinosad, or spinetoram; or
t) Anthranilic diamides, such as flubendiamide, Cyazypyr™ or Rynaxypyr™

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfivazuron or diflubenzuron).

Examples of fungicidal compounds which may be included in the composition of the invention are (E)-N-methyl-2-[2-(2,5-dimethylphenoxymethyl)phenyl]-2-methoxy-iminoacetamide (SSF-129), 4-bromo-2-cyano-N,N-dimethyl-6-trifluoro-methyl-benzimidazole-1-sulphonamide, α-[N-(3-chloro-2,6-xylyl)-2-methoxy-acetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy)-propionamide (AC382042), N-(2-methoxy-5-pyridyl)-cyclo-propane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulphate, copper tallate and Bordeaux mixture, cymoxanil, cyproconazole, cyprodinil, debacarb, di-2-pyridyl disulphide 1,1'-dioxide, dichlofluanid, diclomezine, dicloran, diethofencarb, difenoconazole, difenzoquat, diflumetorim, O,O-di-iso-propyl-S-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)—N-benzyl-N([methyl (methyl-thioethylideneamino-oxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-iso-propyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-Al, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulphur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

Various aspects and embodiments of the present invention will now be illustrated in more detail by way of example. It will be appreciated that modification of detail may be made with out departing from the scope of the invention.

For the avoidance of doubt, where a literary reference, patent application, or patent, is cited within the text of this application, the entire text of said citation is herein incorporated by reference.

EXAMPLES

Example 1

Preparation of Compounds of the Invention

Example 1.1

Preparation of 2-(2-methyl-3-trifluoromethyl-phenoxy)-butyronitrile

A mixture of 2-(methanesulfonyloxy)-butyronitrile (449 mg, 2.75 mmol), 2-methyl-3-trifluoromethylphenol (440 mg, 2.5 mmol), potassium carbonate (432 mg, 3.13 mmol) and potassium iodide (42 mg, 0.25 mmol) in acetonitrile (20 ml) was stirred overnight at 80° C. The mixture was shaken between tBuOMe and water, washed with NaCl (aq. satd) and the ethereal phase dried with $MgSO_4$ and evaporated. The crude product was chromatographed on silica with EtOAc and hexane to give 2-(2-methyl-3-trifluoromethyl-phenoxy)-butyronitrile. 1H-NMR ($CDCl_3$) 1.20 t, 3H; 2.15 dt, 2H; 2.36 s, 3H; 4.75, t, 2H; 7.17, d, 1H; 7.28, t, 1H; 7.37 d, 1H.

Example 1.2

Preparation of 2-[1-(2-methyl-3-trifluoromethyl-phenoxy)-propyl]-4,5-dihydro-1H-imidazole A mixture of 2-(2-methyl-3-trifluoromethyl-phenoxy)-butyronitrile (192 mg, 0.790 mmol), ethylene diamine (0.216 ml, 3.16 mmol) and sodium tetrasulfide (7 mg, 0.04 mmol) was stirred for 4 hrs at 75° C., then cooled and stirred with water (ca 6 ml). The solid was filtered off, washed with water and dried in a vacuum to yield 2-[1-(2-methyl-3-trifluoromethyl-phenoxy)-propyl]-4,5-dihydro-1H-imidazole (m.p. 120-122° C.).

Example 2

Biological Efficacy

This Example illustrates the pesticidal/insecticidal properties of compounds of formula (I). Compounds are identified with respect to the numbers allocated in the tables of characterising data (i.e. Tables 3 and 4). Tests against various pest species were performed as described below.

2.1 *Heliothis virescens* (Tobacco Budworm)

Eggs (0-24 h old) were placed in 24-well microtiter plate on artificial diet and treated with test solutions at an application rate of 200 ppm by pipetting. After an incubation period of 4 days, samples were checked for egg mortality, larval mortality, and growth regulation. The following compounds gave 100% control: 1.016, 1.020 and 1.024. The following compounds gave 80% control: 1.001, 1.003 and 1.022. The following compounds gave 50% control: 1.004, 1.007, and 1.014.

2.2 *Myzus persicae* (Green Peach Aphid)

Sunflower leaf discs were placed on agar in a 24-well microtiter plate and sprayed with test solutions at an application rate of 200 ppm. After drying, the leaf discs were infested with an aphid population of mixed ages. After an incubation period of 6 DAT, samples were checked for mortality. The following compounds gave 100% control: 1.001, 1.003, 1.004, 1.005, 1.006, 1.007, 1.008, 1.016, 1.017, 1.019, 1.021, 1.023 and 1.024. The following compounds gave 80% control: 1.002 and 1.026. The following compounds gave 50% control: 1.010, 1.018, 1.025 and 1.027.

2.3 *Myzus persicae* (Green Peach Aphid)

Roots of pea seedlings, infested with an aphid population of mixed ages, were placed directly in the test solutions of 24 ppm. 6 days after introduction, samples were checked for mortality. The following compounds gave 100% control:

1.001, 1.003, 1.016, 1.021, 1.022 and 1.024. The following compounds gave 80% control: 1.005, 1.019, 1.020 and 1.023.

2.4 *Tetranychus urticae* (Two-Spotted Spider Mite)

Bean leaf discs on agar in 24-well microtiter plates wer sprayed with test solutions at an application rate of 200 ppm. After drying, the leaf discs are infested with mite populations of mixed ages. 8 days later, discs are checked for egg mortality, larval mortality, and adult mortality. The following compounds gave 100% control: 1.001, 1.003, 1.004, 1.005, 1.007, 1.016, 1.021, 1.022, 1.023, and 1.024. The following compounds gave 80% control: 1.019, 1.025 and 1.027.

The invention claimed is:

1. A compound of formula (I):

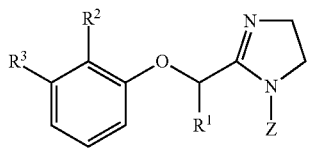

(I)

and the salts and N-oxides thereof, wherein:
$R^1$ is $C_{1-10}$ alkyl;
$R^2$ is $R^2$ is $C_{1-5}$ alkyl, $C_{1-5}$ haloalkyl, $C_{1-5}$ hydroxyalkyl, $C_{2-5}$ alkenyl, $C_{2-5}$ haloalkenyl, $C_{2-5}$ alkynyl, $C_{3-6}$ cycloalkyl, $C_{1-5}$ alkoxy, $C_{1-5}$ haloalkoxy, $C_{1-3}$ alkoxy$(C_{1-3})$alkyl, $C_{1-3}$ alkoxy$(C_{2-3})$alkenyl, $C_{1-5}$ alkylthio, $C_{1-5}$ haloalkylthio, $C_{1-5}$ alkylsulfinyl, $C_{1-5}$ alkylsulfonyl, cyano, nitro, formyl or the group —CH=N—$R^{18}$ wherein $R^{18}$ is hydroxy or $C_{1-3}$ alkoxy;
$R^3$ is $C_{1-5}$haloalkyl;
Z is hydrogen.

2. The compound according to claim 1 wherein $R^3$ is $C_{1-2}$ haloalkyl.

3. The compound according to claim 2, wherein $R^3$ is fluoromethyl, difluoromethyl or trifluoromethyl.

4. The compound according to claim 1, wherein $R^2$ is $C_{1-2}$ alkyl, c-propyl, $C_{1-2}$ haloalkyl, $C_{2-3}$ alkenyl, $C_{2-3}$ haloalkenyl, or the group —CH=N$R^{18}$ wherein $R^{18}$ is hydroxyl or methoxy.

5. The compound according to claim 4, wherein $R^2$ is methyl.

6. An insecticidal, acaricidal, nematicidal or molluscicidal composition comprising a compound, salt or N-oxide according to claim 1, and an inert diluent or carrier.

7. A process for the preparation of a compound of the formula (I) as defined in claim 1, which comprises reacting a compound of the formula (4)

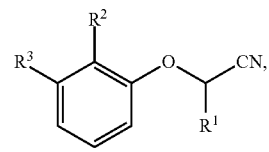

(4)

wherein $R^1$, $R^2$ and $R^3$ are as defined in claim 1, with a diamine of the formula (5)

$H_2NCH_2CH_2NHZ$ (5), wherein Z is as defined in claim 1, in the presence of a catalyst.

8. A method of combating and/or controlling a pest selected from the group consisting of insects, acarids, nematodes and molluscs, which comprises applying to said pest, or to the locus of said pest, or to a plant susceptible to attack by said pest, a compound, N-oxide or salt as defined in claim 1 or a composition as defined in claim 6.

9. A method according to claim 8, wherein said pest is an insect of the order Hemiptera, Lepidoptera, Coleoptera, Thysanoptera, Diptera, Blattodea, Isoptera, Siphonaptera, Hymenoptera, or Orthoptera.

10. A method according to claim 9, wherein said insect is of the order Hemiptera, Lepidoptera, Coleoptera, Thysanoptera or Diptera.

11. A method according to claim 10, wherein said insect is of the order Hemiptera.

12. A method according to claim 9, wherein said insect is of the order Lepidoptera, Thysanoptera, Isoptera, Siphonaptera, Hymenoptera, or Orthoptera.

13. A method according to claim 8, wherein said pest is an acarid.

* * * * *